United States Patent [19]
Normann

[11] 3,974,825
[45] Aug. 17, 1976

[54] REMOTE ELECTRICAL MONITORING OF GAS ACTIVATED BLOOD PUMPS

[75] Inventor: Nils A. Normann, Houston, Tex.

[73] Assignee: Baylor College of Medicine, Houston, Tex.

[22] Filed: Oct. 1, 1975

[21] Appl. No.: 618,718

[52] U.S. Cl. .................................. 128/1 D; 3/1.7; 128/2.05 V; 128/2.1 A; 324/61 R; 331/117 R
[51] Int. Cl.$^2$ ........................................ A61F 1/24
[58] Field of Search ......... 128/1 D, 2 P, 2 R, 2.1 A, 128/DIG. 3, 25, 2.05 V; 3/1.7; 73/194 R, 262; 417/20, 212, 274; 324/61 R, 61 QS; 331/106, 116 M, 117 R

[56] References Cited
UNITED STATES PATENTS

| | | | |
|---|---|---|---|
| 2,452,799 | 11/1948 | Speaker et al. | 128/2.05 V |
| 2,823,312 | 2/1958 | Keonjian | 331/117 |
| 3,491,377 | 1/1970 | Bolie | 128/1 D |
| 3,531,257 | 9/1970 | Harvey et al. | 324/61 R |
| 3,650,093 | 3/1972 | Rosenberg | 128/214.2 |
| 3,718,044 | 2/1973 | Joyce, Jr. et al. | 3/1.7 |
| 3,720,199 | 3/1973 | Rishton | 128/1 D |
| 3,783,453 | 1/1974 | Bolie | 128/1 D |

Primary Examiner—William E. Kamm
Attorney, Agent, or Firm—Fulbright & Jaworski

[57] ABSTRACT

An electrical capacitance measurement system for monitoring at a distance the instantaneous blood volume within the body of an air or gas activated blood pump. Electrical capacitance changes within the pneumatic blood pump frequency modulates an oscillator, and the extraneous capacitances encountered are incorporated as electrical, integral components in oscillator operation. An inductor, placed within or in close proximity to the pump, and the relatively small electrical capacitance within the pump form an oscillator tank which primarily determines oscillator frequency. By thus creating a tank at the site of measurement, active and other oscillator components can be placed at a distance from the pump, and undesirable cable capacitances can conveniently be incorporated as participating feedback capacitors. Preferably, an electrically protective shield is attached to the outside of the pump which electrically shields the pump and which provides a capacitance larger than the sensing capacitance to provide a linear relationship between the sensing capacitance and the sensor output. The Clapp oscillator principle has been employed as it permits the separate location of the sensing, frequency determining tank, and, at the same time it provides high sensitivity for capacitance measurement and adequate long-term stability. The present system is applicable to various types of gas activated blood pumps employed outside or inside the body of humans or animals.

8 Claims, 4 Drawing Figures

REMOTE ELECTRICAL MONITORING OF GAS ACTIVATED BLOOD PUMPS

BACKGROUND OF THE INVENTION

This invention was conceived in the course of the execution of a grant from the National Heart and Lung Institute. With the exception of nuclear powered pumps and standard roller-pumps, both clinically and experimentally used blood pumps are, at the present time, routinely energized from a pneumatic power source. The pumps may be biventricular, intended for total heart replacement, or, they consist of a single ventricle intended for use as an auxiliary pump assisting the natural heart, usually the left side of the heart. If these pumps are to function optimally, there is a need for precise, instantaneous measurement of blood volume within the pump. Such a monitoring system should provide (1) direct, on-line monitoring of dynamic pump behavior, including magnitude of displacement and rates of filling and ejection, and (2) the means for closed loop, automatic control of pump operation. The need for such a monitoring system is particularly great if a pump is implanted inside the body as this excludes visual observations. These needs have not previously been met.

The measurement of a varying capacitance between two plates is a common method for measuring displacement, for instance, in a displacement or in a pressure transducer. The principle is applicable to pneumatic blood pumps, as described in Vol. XII, No. 1, pages 3–12, Cardiovascular Research Center Bulletin, 1974, since they contain, within a relatively rigid housing, two compartments separated by a flexible diaphragm or bladder wall. Since one compartment contains blood and the other gas, such as air, expansion of one compartment at the expense of the other will, conceptually, change the electrical capacitance across the pump, the dielectric constant of blood being much greater than that of air or gas. The device here described utilizes this fact. In the practical application to pneumatic blood pumps, it has been found expedient and advantageous to monitor not the capacitance across the pump, but rather the capacitance across the gas (air) space as this varies reciprocally with instantaneous blood volume within the pump. The capacitance to be measured ranges from a fraction of a picofarad (pf) in some pumps to a maximum of 30–40 pf in other pumps.

Theoretically, the simplest way to measure the relatively small electrical pump capacitances is to attach appropriate electronic circuitry directly to or inside the pump. In practice, this arrangement has several drawbacks, the most important being the problem of long-term reliability and electrical stability. The problem is compounded if the pump is implanted inside the body: (1) body fluids represent a hostile environment for electronic circuitry; (2) space is frequently at a premium; (3) electronics are inaccessible; the replacement of a sense module would require additional surgery; (4) if telemetry is utilized, implantation of a power source creates additional space, encapsulation, and duration problems.

The following specifications and requirements of a pneumatic blood pump monitoring system are incorporated in the present invention: (1) all active electronic components and circuitry can be located at a convenient distance (12 feet or more) from the pump; (2) it can easily be adapted to various pump configurations; (3) it can be employed with implanted pumps without requiring separate transcutaneous (across-the-skin) cable channel; (4) it electronically provides (a) on-line direct readout of the instantaneous blood volume within the pump; (b) output which can be displayed in analog form on oscilloscope or standard recorder; (c) output which can be utilized in closed loop, beat-to-beat, automatic control of pump operation; (d) good signal-to-noise ratio; (e) long-term stability; (f) high immunity to interference.

SUMMARY

The present invention provides an electrical capacitance method for remote monitoring of instantaneous blood volume within gas activated blood pumps.

The present solution for remote, instantaneous measurement of electrical capacitance within pneumatic blood pumps is effective, and is based on the following concepts: (1) utilization of an oscillator circuit in which the capacitance sensing, frequency determining tank is located within or in close proximity to the pump; (2) remote location of active and other electronic components made practical by the incorporation of extraneous, undesirable, relatively large capacitance (typically that of a relatively long, connecting shielded cable) as integral components in an oscillator circuit; (3) the employment of an oscillator circuit, incorporating the above (1) and (2), which will additionally provide high sensitivity to the small capacitance and capacitance changes within the pump, and, at the same time, be characterized by adequate long-term stability. These concepts are implemented by an adaptation of the Clapp oscillator principle.

Briefly, included among the reasons for having the frequency modulated sensor oscillator remote, i.e., at a distance from the pump, are (1) to secure long-term reliability and stability; (2) to facilitate replacement or switching to back-up units; (3) to facilitate application to various types of pneumatic blood pumps; (4) to make the sensor system suitable for use in conjunction with body implanted pumps.

It is, therefore, an object of the present invention to provide a device for remote measurement of instantaneous blood volume within pneumatic blood pumps.

Another object of the present invention is the provision of such a device wherein undesirable effects of extraneous capacitances encountered are minimized or avoided by placing the sensing, frequency determining tank of an oscillator within or in close proximity to the pump.

Still another object of the present invention is the provision of such a device wherein the undesirable effects of extraneous capacitances encountered are minimized or avoided by incorporating these capacitances as integral components in an oscillator circuit instead of trying to compensate for them.

Still another object of the present invention is the provision of such a device which is highly sensitive to capacitance frequency modulation.

Still another object of the present invention is the provision of such a device with a high oscillator stability.

Still another object of the present invention is the provision of a device for instantaneous measurement of blood volume within implanted pneumatic blood pumps in which the electronics are located outside the body, rather than in the hostile environment of the body or within the implanted pump where space is at a premium.

A further object of the present invention is the provision of an electrically protective shield on the outside of the pump which will electrically shield the pump and will provide a capacitance larger than the sensing capacitance to provide a more linear relationship between the sensing capacitance and the sensor output.

A further object of the present invention is the provision of such a device wherein access to the electronics is easy and advantageous, and substitute backup modules can easily be activated.

Still other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

In the drawings forming a part of the disclosure herein, like character references designate like parts throughout the several views, wherein.

DESCRIPTION OF THE PREFERRED EMBODIMENT

The present invention provides a device for remote measurement of instantaneous blood volume within gas activated blood pumps.

Although frequency modulation of an oscillator constitutes one of the standard methods for measuring capacitance, the presently described device for "remote" sensing of such capacitance is a new improvement. Placing a sensing oscillator itself in close proximity to the capacitance to be measured will minimize cable problems; however, it is preferable to have the electronics remote for the following reasons:

1. Electronics inside, attached to, or in close proximity to a mechanical device, such as a pneumatic blood pump, have the following drawbacks: (a) in long-term use it is likely to suffer with respect to reliability and stability; (b) space inside the pump is likely to be at a premium; (c) access to electronics, eventual replacement, is cumbersome at best, impossible at worst; (d) the above drawbacks are compounded if the pump is implanted in the body; (e) inside the body, tissue fluids constitute a hostile environment for implanted electronics.

2. By remote location of electronics, the above problems are circumvented.

3. Although a capacitance sensing, frequency modulated oscillator will function as an FM transmitter, remote location of electronics using cable connection, as opposed to telemetry, requires minimal modification of the pump and eliminates long-term power and, eventually, implant problems.

4. The present device requires only a thin, shielded cable (1 mm diameter or less) connection with the pump. Incorporated in or within the pneumatic tubing (the presence of which is a necessity), the cable does not introduce additional complexity, a factor particularly important if the pump is implanted.

5. Remote location of electronic sense module (device) provides easy access to the contained electronics.

6. Remotely located sensing module lends itself for easy switching to a back-up unit in the event of failure.

Figure 1:
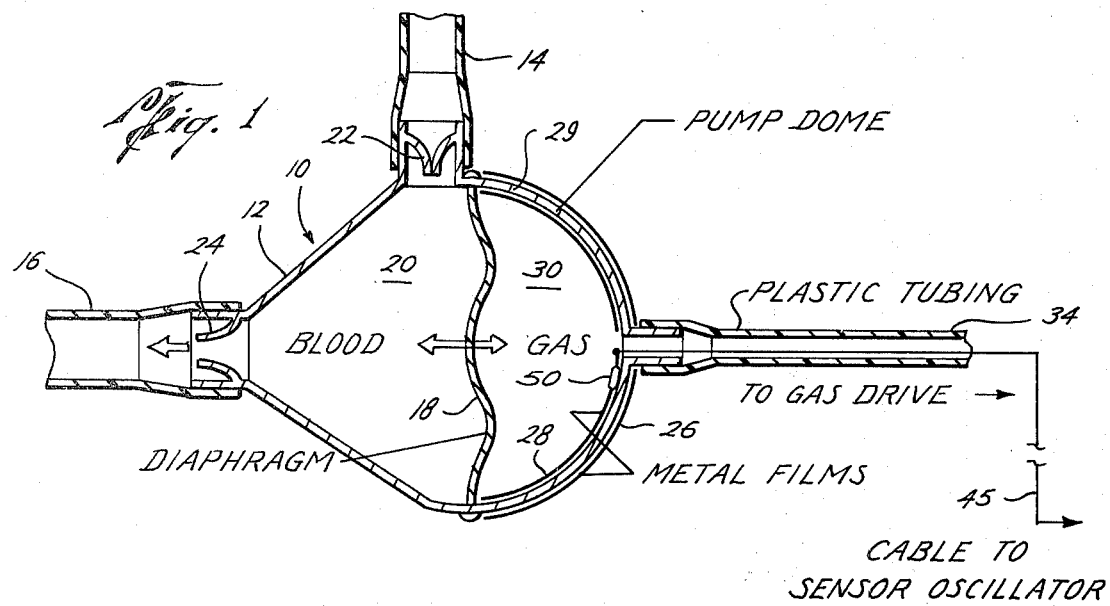
FIG. 1 is a cross-sectional view of a diaphragm-type pneumatic blood pump.

Referring now to FIG. 1, the reference numeral 10 generally indicates a blood pump for use, for example only, in the left ventricular bypass of the human heart. The pump 10 generally includes a housing 12 having a blood inlet 14 and a blood outlet 16, and a flexible member 18, such as a diaphragm or bladder, which forms a blood containing compartment 20. Pumping is achieved by introducing periodic pulses of a gas, such as air or carbon dioxide, in the air space 30 against a flexible member 18, thus causing blood ejection out of and entry into the blood compartment 20 by means of check valves 22 and 24 positioned in the inlet 14 and the outlet 16, respectively.

Shown in FIG. 1 are some of the items involved in the application of the capacitance method for remote measurement of blood volume within the pump 10. One or more metallic films on the inner surface of dome 29 may serve as capacitor "plate" or "plates". In the presently preferred embodiment, one continuous metallic film or plate 28 is applied to the inner surface of the dome 29, and the flexible interface, such as diaphragm 18, serves as the other plate in a variable capacitor. In this configuration, blood and body tissues provide the high frequency current return path via circuit "ground". This is indicated schematically by the variable capacitor 32 in FIG. 2. Capacitance across air space 30 varies with volume of blood in the space 20.

A second capacitance exists between the inside of the pump and the outside of the pump across the pump wall 29. Preferably, a second film 26, attached to the outside of dome 29, forms a fixed capacitor with the inner film 28. The second film 26 is connected to circuit ground and serves as a pump shielding. Since thus the electrical relationship of inner, sensing plate 28 is fixed relative to ground, i.e., relative to the outside medium, the pump can be handled without interferring with sensing function, and, importantly, the pump can be surrounded by an electrically conducting medium as is the case when a pump is implanted in the body. The fixed capacitor between inner 28 and outer metallic films 26 is represented schematically by capacitor 36 in FIG. 2, in parallel with the variable, sensing capacitor 32.

Figure 2:
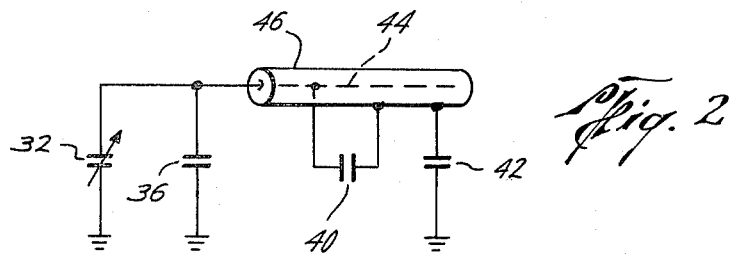
FIG. 2 is an electrical schematic of the various capacitances which must be considered in the present invention.

In FIG. 1, a connecting cable 45 enters the gas space 30 via the gas or pneumatic supply line 34. In close proximity to the pump or within, the central conductor 44 or wire of cable 45 is connected to a small inductor 50 (typically 100 microhenry), the other end of which is electrically connected to the inner metallic film 28. In FIG. 2, the cable capacitance (typically 30 pF/ft) between wire 44 and the cover or shield 46 of cable 45 is represented by capacitor 40, and capacitance between shield 46 and ground (if shield is not grounded) is represented by capacitor 42.

In order to minimize the effects of the extraneous capacitances 36, 40 and 42, the present design is based on the following concepts: (1) an arrangement by which the sensing, frequency determining "tank", consisting of capacitor 32, 36, and inductor 50, is located in the pump; (2) the incorporation of the extraneous capacitances 40 and 42 as integral components in a high frequency, (typically 900 KHz) oscillator. Additionally, it is required that the circuit provides high sensitivity to changes in capacitance 32, in the presence of capacitance 36, combined with adequate long-term stability. These concepts are implemented by employing the Clapp oscillator principle as indicated in FIG. 3.

First, and most importantly, an inductor 50 is connected adjacent to or within the pump 10 and connected to the capacitances 32 and 36 to form the frequency determining tank of the oscillator 54. The wire 44 is then connected between the inductor 50 and, capacitively coupled, to a transistor, generally indicated by the reference 52, of the oscillator 54. The third and fourth (cable) capacitances 40 and 42 are connected, as will be fully described hereinafter, to participate as feedback capacitors in the Clapp type oscillator 54.

The main frequency determining capacitors will be the first and second capacitors 32 and 36. Variations in the first, or sensing, capacitor 32 will cause a relatively large frequency deviation in spite of the attenuating effect of the second capacitor 36. For example, at an oscillator frequency of 900 KHz, a 4% frequency deviation can typically be obtained from a pump stroke volume of 100 ml. It should be noted that a high ratio between the second and first capacitors 36 and 32 will increase the linearity between capacitance change (pump displacement) and sensor output. Depending on pump configuration, it may thus be advantageous to intentionally increase the value of capacitor 36 with an additional component capacitor 37 and still maintain good sensitivity.

Figure 3:
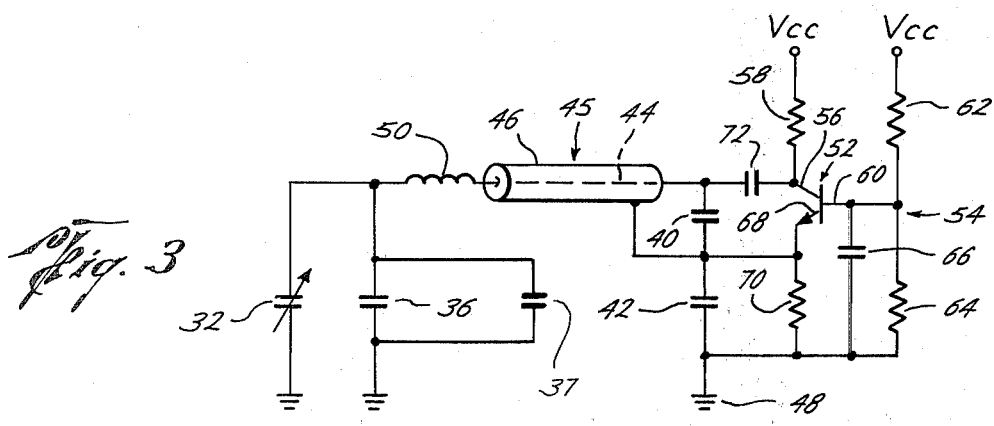
FIG. 3 is an electrical schematic of an oscillator circuit in which the sensing, frequency determining tank is located in or adjacent to the pump, and undesirable pump and cable capacitances are incorporated as integral circuit components.

Describing the electrical network of FIG. 3 in more detail, oscillator 54 may include an N-P-N transistor 52. Connected between the collector 56 of the transistor and the collector supply voltage (designated Vcc) is a first resistor 58. Connected between base 60 of the transistor and Vcc is second resistor 62. A third resistor 64 and a fifth capacitor 66 are connected in parallel between the base 60 of the transistor and the ground 48. Connected between the emitter 68 of the transistor and ground 48 is a fourth resistor 70. Functionally connected in parallel, with one side grounded, are the first capacitor 32 which is the pump capacitance to be measured, and the second, or shunting, capacitor 36, consisting of capacitance between inner and outer metallic films. Connected to the common, non-grounded side of the first 32 and second capacitors 36 is the inductor 50 which is located adjacent to or within the pump 10. Such placement of the inductor 50 results (1) in a position of the frequency determining tank separate from that of the rest of the oscillator, and (2) in the inclusion of the third and fourth capacitors 40 and 42 in the capacitor feedback network of the oscillator. The third capacitor 40 represents the capacitance between the wire 44 and the cover, or "shield" 46 (usually connected in parallel with a component capacitor), while the fourth capacitor 42 represents the capacitance between the cover 46 and ground 48 (usually in parallel with a component capacitor). The third capacitance 40 and the fourth capacitance 42, connected in series, are connected via coupling capacitor 72 to collector 56. The emitter 68 of the transistor 52 is connected to the common junction of feedback capacitors 40 and 42.

The effect of the relatively large third and fourth capacitors 40 and 42 on oscillator frequency is relatively small because of the in series configuration of the frequency determining tank which incorporates the much smaller first and second capacitors 32 and 36. By placing the inductor 50 within, or in close proximity to, the pump, the capacitance sensing and frequency determining tank is in the pump itself, and the cable 45 connecting the tank to the remote oscillator functions, electrically, as integral oscillator components—with relatively little effect on oscillator frequency.

Figure 4:
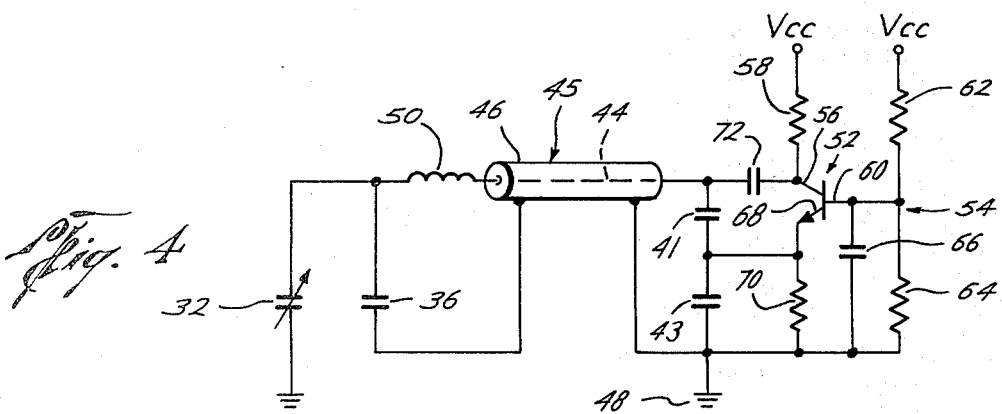
FIG. 4 is an electrical schematic of a modified oscillator circuit which may be utilized if the cable is relatively short.

It should be noted that the most essential feature in this design is the location of the capacitance (or inductance) sensing, frequency determining tank at the site of measurement. In the application of monitoring pneumatic blood pumps, the here described cable connections are preferable if cable length exceeds approximately 12 feet. If a cable shorter than 12 feet is utilized, the cable capacitances are less of a problem and the circuit may be modified, as best seen in FIG. 4, in which the oscillator end of the shield 46 may be connected directly to circuit ground, and, at the pump end, to outer metal film 28 (capacitor 36). In this configuration, cable capacitance represents a shunt across oscillator component capacitors 41 and 43, and device objectives are equally well attained.

The present invention, therefore, is well adapted to carry out the objects and attain the ends and advantages mentioned as well as others therein, as it has been demonstrated experimentally in the application to pneumatic blood pumps, employed both outside and inside the body of calves. While a presently preferred embodiment of the invention has been given for the purpose of disclosure, numerous changes may be made without departing from the spirit and scope of the invention as hereinafter claimed.

What is claimed is:
1. In a blood pump having a flexible member actuated by gas through a conduit for pumping blood through the pump in which the internal electrical capacitance in the pump varies in accordance with the position of the flexible member, the improvement in an electrical capacitance measuring system using a Clapp type oscillator having a tank circuit separate from the oscillator proper and having the electrical connection between them incorporated as component capacitors in the oscillator for measuring the instantaneous position of the flexible member comprising,
   said internal electrical capacitance of the pump forming a portion of the tank circuit, and frequency modulating the oscillator,
   the electrical capacitance between the inside of the pump and the outside of the pump, across the pump wall, being functionally connected in parallel to the electrical capacitance of the pump,
   an inductor connected in series with the internal electrical capacitance and the electrical capacitance between the pump inside and the pump outside, and
   a cable having an electrically conducting cover and an inside wire connected to the inductor, the capacitance between the wire and the cover, and the capacitance between the cover and ground forming feedback capacitors of said oscillator.

2. The apparatus of claim 1 wherein the electrical capacitance between the inside of the pump and the outside of the pump is formed by an electrically conductive film on the inside of the pump and by an electrically protective shield on the outside of the pump.

3. The apparatus of claim 1 wherein said inductor is positioned adjacent the pump and the cable extends away from the pump for connection to the remaining components of the oscillator circuit located remotely from the pump.

4. The apparatus of claim 3 wherein the cable is positioned within a portion of the gas conduit.

5. In an electrical capacitance system for remote monitoring of instantaneous blood volume within a pneumatic blood pump having a flexible member actuated by gas and employing a Clapp type oscillator which includes a transistor, the improvement of a measuring system for monitoring and control of pump operation and measuring the volume of blood pumped by the blood pump including,
   a first capacitance, one plate of which is formed by an electrically conducting film inside the pump and the other plate of which is formed by blood, flexible member, and gas interface connected to circuit ground through the blood, and which varies with the volume of blood flowing into and out from the pump, and is the unknown to be measured,
   a second capacitance existing between the electrically conducting film and the outside of the pump and which shunts the first capacitor, is connected in parallel with such first capacitance, and is of a larger value than the first capacitance,
   an inductor connected to the common ungrounded side of the first and second capacitances,
   an electrical cable having a wire and an electrically conducting cover providing a third capacitance between the wire and the cover and providing a fourth capacitance between the cover and the ground,
   the third capacitance connected between the emitter and a capacitor connected to the collector of the transistor of the Clapp type oscillator, and
   the fourth capacitance connected between the transistor's emitter and ground.

6. In a blood pump having a flexible member actuated by gas through a conduit for pumping blood through the pump in which the internal electrical capacitance in the pump varies in accordance with the position of the flexible member, the improvement in an electrical capacitance measuring system using a Clapp type oscillator having a tank circuit comprising,
   said internal electrical capacitance of the pump forming a portion of the tank circuit,
   an electrically protective shield on the outside of the pump forming an electrical capacitance with the inside of the pump and connected in parallel to the electrical capacitance of the pump,
   an inductor positioned adjacent the pump and connected in series with the internal electrical capacitance of the pump and the shield forming the tank circuit,
   a cable having an electrically conducting cover and an inside wire connected to the inductor and extending away from the pump through a portion of the gas conduit to the remaining components of the oscillator located at a position spaced from the pump,
   the capacitance between the wire and the cover of the cable, and the capacitance between the cover of the cable and ground forming feedback capacitors of said oscillator.

7. The apparatus of claim 6 wherein the capacitance formed between the inside of the pump and the protective shield is larger than the internal electrical capacitance of the pump and is in combination with a parallel capacitor for providing a substantially linear relationship between changes in the pump internal capacitance and the oscillator output.

8. In a blood pump having a flexible member actuated by gas through a conduit for pumping blood through the pump in which the internal electrical capacitance in the pump, one plate of which is formed by an electrically conducting film and the other plate of which is formed by the blood flexible member and gas, varies in accordance with the position of the flexible member, the improvement in an electrical capacitance measuring system using a Clapp type oscillator having a tank circuit separate from the oscillator proper for measuring the instantaneous position of the flexible member comprising,
   said internal electrical capacitance in the pump forming a portion of the tank circuit, and frequency modulating the oscillator,
   an electrically protective shield on the outside of the pump, and the electrical capacitance formed between the electrically conducting film on the inside of the pump and the electrically protective shield being functionally connected in parallel to the internal electrical capacitance,
   an inductor connected in series with the internal electrical capacitance and the electrical capacitance formed between the film and the shield,
   a cable having an electrically conducting cover and an inside wire connected between the inductor and the oscillator, the cover of the oscillator end of the cable being connected directly to ground, and the cover of the pump end of the cable being connected to the electrically protective shield.

* * * * *